United States Patent
Dugan et al.

(10) Patent No.: US 10,080,518 B2
(45) Date of Patent: Sep. 25, 2018

(54) METHODS AND APPARATUS FOR ENCOURAGING WAKEFULNESS OF A DRIVER USING BIOMETRIC PARAMETERS MEASURED USING A WEARABLE MONITOR

(71) Applicants: Brian M. Dugan, Sleepy Hollow, NY (US); Valerie G. Dugan, Sleepy Hollow, NY (US)

(72) Inventors: Brian M. Dugan, Sleepy Hollow, NY (US); Valerie G. Dugan, Sleepy Hollow, NY (US)

(*) Notice: Subject to any disclaimer, the term of this patent is extended or adjusted under 35 U.S.C. 154(b) by 0 days.

(21) Appl. No.: 14/467,041

(22) Filed: Aug. 24, 2014

(65) Prior Publication Data
US 2014/0364752 A1    Dec. 11, 2014

Related U.S. Application Data

(63) Continuation of application No. 14/297,123, filed on Jun. 5, 2014, now Pat. No. 9,687,188, which is a
(Continued)

(51) Int. Cl.
*A61B 5/04* (2006.01)
*A61B 5/18* (2006.01)
(Continued)

(52) U.S. Cl.
CPC .............. *A61B 5/18* (2013.01); *A61B 5/0002* (2013.01); *A61B 5/0004* (2013.01);
(Continued)

(58) Field of Classification Search
CPC ....... A61B 5/00; A61B 5/0002; A61B 5/0004; A61B 5/0006; A61B 5/0008; A61B 5/002;
(Continued)

(56) References Cited

U.S. PATENT DOCUMENTS 3,834,702 A    9/1974  Bliss
4,484,743 A   11/1984  Williams
(Continued)

FOREIGN PATENT DOCUMENTS

EP    1 292 217 B1    11/2005
EP    1 639 939        3/2006
(Continued)

OTHER PUBLICATIONS

Non-Final Office Action of U.S. Appl. No. 14/297,123 dated Oct. 30, 2015.
(Continued)

*Primary Examiner* — Eric D. Bertram
*Assistant Examiner* — Elizabeth K So
(74) *Attorney, Agent, or Firm* — Dugan & Dugan, PC

(57) ABSTRACT

In a first aspect, a method is provided for determining a level of wakefulness of a driver of a vehicle using a mobile telephone. The method includes (a) employing a wearable monitor to detect a biometric parameter of a user while the user is driving a vehicle; (b) communicating biometric parameter information from the wearable monitor to a mobile telephone of the user while the user is driving the vehicle; (c) employing the mobile telephone to obtain a level of wakefulness of the user while the user is driving the vehicle, the level of wakefulness of the user being determined based on biometric parameter information received from the wearable monitor; and (d) if the level of wakefulness determined for the user is below a predetermined level of wakefulness, employing the mobile telephone to attempt to increase the level of wakefulness of the user. Numerous other aspects are provided.

21 Claims, 6 Drawing Sheets

Related U.S. Application Data continuation of application No. 11/768,167, filed on Jun. 25, 2007, now Pat. No. 8,781,568.

(60) Provisional application No. 60/805,726, filed on Jun. 23, 2006, provisional application No. 60/805,838, filed on Jun. 26, 2006.

(51) Int. Cl.
*A61B 5/024* (2006.01)
*H04W 48/04* (2009.01)
*A61B 5/16* (2006.01)
*A61B 5/00* (2006.01)

(52) U.S. Cl.
CPC .......... *A61B 5/0015* (2013.01); *A61B 5/0022* (2013.01); *A61B 5/024* (2013.01); *A61B 5/02438* (2013.01); *A61B 5/02444* (2013.01); *A61B 5/165* (2013.01); *A61B 5/486* (2013.01); *A61B 5/6802* (2013.01); *A61B 5/6824* (2013.01); *A61B 5/6898* (2013.01); *A61B 5/7278* (2013.01); *A61B 5/7282* (2013.01); *A61B 5/742* (2013.01); *A61B 5/746* (2013.01); *A61B 5/747* (2013.01); *H04W 48/04* (2013.01); *A61B 5/681* (2013.01)

(58) Field of Classification Search
CPC ... A61B 5/0022; A61B 5/0024; A61B 5/0026; A61B 5/0048; A61B 5/0059; A61B 5/024; A61B 5/02405; A61B 5/026; A61B 5/03; A61B 5/04; A61B 5/04001; A61B 5/04002; A61B 5/04004; A61B 5/0404
USPC .......................... 600/386, 388, 389, 390, 391
See application file for complete search history.

(56) References Cited

U.S. PATENT DOCUMENTS

| | | |
|---|---|---|
| 4,542,897 A | 9/1985 | Melton et al. |
| 4,735,410 A | 4/1988 | Nobuta |
| 4,817,938 A | 4/1989 | Nakao et al. |
| 4,858,930 A | 8/1989 | Sato |
| 4,976,435 A | 12/1990 | Shatford et al. |
| 5,001,632 A | 3/1991 | Hall-Tipping |
| 5,142,358 A | 8/1992 | Jason |
| RE34,728 E | 9/1994 | Hall-Tipping |
| 5,362,069 A | 11/1994 | Hall-Tipping |
| 5,377,100 A | 12/1994 | Pope et al. |
| 5,462,504 A | 10/1995 | Trulaske et al. |
| 5,515,865 A | 5/1996 | Scanlon |
| 5,527,239 A | 6/1996 | Abbondanza |
| 5,591,104 A | 1/1997 | Andrus et al. |
| 5,592,401 A | 1/1997 | Kramer |
| 5,624,316 A | 4/1997 | Roskowski et al. |
| 5,645,513 A | 7/1997 | Haydocy et al. |
| 5,667,459 A | 9/1997 | Su |
| 5,672,107 A | 9/1997 | Clayman |
| 5,702,323 A | 12/1997 | Poulton |
| 5,781,698 A | 7/1998 | Teller et al. |
| 5,885,156 A | 3/1999 | Toyohara et al. |
| 5,902,250 A | 5/1999 | Verrier et al. |
| 5,918,603 A | 7/1999 | Brown |
| 5,928,133 A | 7/1999 | Halyak |
| 5,947,868 A | 9/1999 | Dugan |
| 6,024,675 A | 2/2000 | Kashiwaguchi |
| 6,062,216 A | 5/2000 | Corn |
| 6,066,075 A | 5/2000 | Poulton |
| 6,152,856 A | 11/2000 | Studor et al. |
| 6,179,713 B1 | 1/2001 | James et al. |
| D439,981 S | 4/2001 | Kasabach et al. |
| 6,213,872 B1 | 4/2001 | Harada et al. |
| 6,244,988 B1 | 6/2001 | Delman |
| 6,251,010 B1 | 6/2001 | Tajiri et al. |
| 6,267,677 B1 | 7/2001 | Tajiri et al. |
| 6,302,789 B2 | 10/2001 | Harada et al. |
| D451,604 S | 12/2001 | Kasabach et al. |
| 6,347,993 B1 | 2/2002 | Kondo et al. |
| 6,354,940 B1 | 3/2002 | Itou et al. |
| 6,375,572 B1 | 4/2002 | Masuyama et al. |
| D460,971 S | 7/2002 | Sica et al. |
| 6,456,749 B1 | 9/2002 | Kasabach et al. |
| 6,482,092 B1 | 11/2002 | Tajiri et al. |
| 6,494,830 B1 | 12/2002 | Wessel |
| 6,513,160 B2 | 1/2003 | Dureau |
| 6,514,199 B1 | 2/2003 | Alessandri |
| 6,527,711 B1 | 3/2003 | Stivoric et al. |
| 6,579,231 B1 | 6/2003 | Phipps |
| 6,585,622 B1 | 7/2003 | Shum et al. |
| 6,595,858 B1 | 7/2003 | Tajiri et al. |
| 6,595,929 B2 | 7/2003 | Stivoric et al. |
| 6,605,038 B1 | 8/2003 | Teller et al. |
| 6,628,847 B1 | 9/2003 | Kasabach et al. |
| 6,641,482 B2 | 11/2003 | Masuyama et al. |
| 6,652,383 B1 | 11/2003 | Sonoda et al. |
| 6,705,972 B1 | 3/2004 | Takano et al. |
| 6,720,983 B1 | 4/2004 | Massaro et al. |
| 6,746,371 B1 | 6/2004 | Brown et al. |
| 6,758,746 B1 | 7/2004 | Hunter et al. |
| 6,786,825 B2 | 9/2004 | Kawazu |
| 6,796,927 B2 | 9/2004 | Toyama |
| 6,881,176 B2 | 4/2005 | Oishi et al. |
| 6,888,779 B2 | 5/2005 | Mollicone et al. |
| 6,902,513 B1 | 6/2005 | McClure |
| 6,966,837 B1 | 11/2005 | Best |
| 7,020,508 B2 | 3/2006 | Stivoric et al. |
| 7,027,621 B1* | 4/2006 | Prokoski .......... G06K 9/00255 |
| | | 180/272 |
| 7,041,049 B1 | 5/2006 | Raniere |
| 7,057,551 B1 | 6/2006 | Vogt |
| 7,068,860 B2 | 6/2006 | Kasabach et al. |
| 7,153,262 B2 | 12/2006 | Stivoric et al. |
| 7,261,690 B2 | 8/2007 | Teller et al. |
| 7,285,090 B2 | 10/2007 | Stivoric et al. |
| 7,628,730 B1 | 12/2009 | Watterson et al. |
| 7,749,056 B2 | 7/2010 | Ando et al. |
| 7,931,563 B2 | 4/2011 | Shaw et al. |
| 7,934,983 B1 | 5/2011 | Eisner |
| 7,946,959 B2 | 5/2011 | Shum et al. |
| 8,188,868 B2 | 5/2012 | Case, Jr. |
| 8,287,436 B2 | 10/2012 | Shum et al. |
| 8,313,416 B2 | 11/2012 | Ellis et al. |
| 8,556,778 B1 | 10/2013 | Dugan |
| 2001/0015123 A1 | 8/2001 | Nishitani et al. |
| 2002/0019685 A1 | 2/2002 | Ries-Mueller |
| 2002/0022516 A1 | 2/2002 | Forden |
| 2002/0080035 A1 | 6/2002 | Youdenko |
| 2002/0082065 A1 | 6/2002 | Fogel et al. |
| 2002/0082077 A1 | 6/2002 | Johnson et al. |
| 2002/0090985 A1 | 7/2002 | Tochner et al. |
| 2002/0151992 A1 | 10/2002 | Hoffberg et al. |
| 2002/0160883 A1 | 10/2002 | Dugan |
| 2002/0163495 A1 | 11/2002 | Doynov |
| 2003/0224337 A1 | 12/2003 | Shum et al. |
| 2004/0023761 A1 | 2/2004 | Emery |
| 2004/0049132 A1 | 3/2004 | Barron et al. |
| 2004/0053690 A1 | 3/2004 | Fogel et al. |
| 2004/0176083 A1 | 9/2004 | Shiao |
| 2004/0209594 A1 | 10/2004 | Naboulsi |
| 2004/0260440 A1* | 12/2004 | Fujita .................... G08B 21/06 |
| | | 701/36 |
| 2005/0068169 A1 | 3/2005 | Copley et al. |
| 2005/0101845 A1 | 5/2005 | Nihtila |
| 2005/0113703 A1* | 5/2005 | Farringdon .......... A61B 5/0428 |
| | | 600/509 |
| 2005/0177051 A1 | 8/2005 | Almen |
| 2005/0275541 A1 | 12/2005 | Sengupta et al. |
| 2006/0025282 A1 | 2/2006 | Redmann |
| 2006/0031102 A1 | 2/2006 | Teller et al. |
| 2006/0089543 A1 | 4/2006 | Kim et al. |
| 2006/0122474 A1 | 6/2006 | Teller et al. |
| 2006/0224051 A1 | 10/2006 | Teller et al. |
| 2006/0264730 A1 | 11/2006 | Stivoric et al. |

(56) References Cited

U.S. PATENT DOCUMENTS

| | | |
|---|---|---|
| 2006/0281543 A1 | 12/2006 | Sutton et al. |
| 2007/0001828 A1 | 1/2007 | Martinez |
| 2007/0004482 A1 | 1/2007 | Ando et al. |
| 2007/0035384 A1 | 2/2007 | Belcher |
| 2007/0038038 A1 | 2/2007 | Stivoric et al. |
| 2007/0053513 A1 | 3/2007 | Hoffberg |
| 2007/0072616 A1 | 3/2007 | Irani |
| 2007/0111858 A1 | 5/2007 | Dugan |
| 2007/0167204 A1 | 7/2007 | Lyle et al. |
| 2007/0173705 A1 | 7/2007 | Teller et al. |
| 2007/0197274 A1 | 8/2007 | Dugan |
| 2007/0208233 A1 | 9/2007 | Kovacs |
| 2007/0260482 A1 | 11/2007 | Nurmela et al. |
| 2008/0027337 A1 | 1/2008 | Dugan et al. |
| 2008/0094226 A1 | 4/2008 | O'Shea et al. |
| 2008/0129518 A1 | 6/2008 | Carlton-Foss |
| 2008/0146892 A1 | 6/2008 | LeBoeuf et al. |
| 2008/0167861 A1 | 7/2008 | Inoue et al. |
| 2008/0191864 A1 | 8/2008 | Wolfson |
| 2008/0218310 A1 | 9/2008 | Alten et al. |
| 2008/0281633 A1 | 11/2008 | Burdea et al. |
| 2008/0318679 A1 | 12/2008 | Tran et al. |
| 2009/0005140 A1 | 1/2009 | Rose et al. |
| 2009/0121894 A1 | 5/2009 | Wilson et al. |
| 2009/0270743 A1 | 10/2009 | Dugan et al. |
| 2010/0033303 A1 | 2/2010 | Dugan et al. |
| 2010/0160041 A1 | 6/2010 | Grant et al. |
| 2010/0240458 A1 | 9/2010 | Gaiba et al. |
| 2010/0287011 A1 | 11/2010 | Muchkaev |
| 2011/0065504 A1 | 3/2011 | Dugan et al. |
| 2011/0082008 A1 | 4/2011 | Cheung et al. |
| 2011/0190055 A1 | 8/2011 | Leyvand et al. |
| 2011/0260830 A1 | 10/2011 | Weising |
| 2011/0275483 A1 | 11/2011 | Dugan et al. |
| 2012/0208676 A1 | 8/2012 | Shum et al. |
| 2012/0252580 A1 | 10/2012 | Dugan |
| 2012/0253487 A1 | 10/2012 | Dugan |
| 2012/0253489 A1 | 10/2012 | Dugan |
| 2012/0306643 A1 | 12/2012 | Dugan |
| 2013/0252731 A1 | 9/2013 | Dugan et al. |
| 2014/0011640 A1 | 1/2014 | Dugan |

FOREIGN PATENT DOCUMENTS

| | | |
|---|---|---|
| EP | 1 292 218 B1 | 4/2006 |
| EP | 1 702 560 | 9/2006 |
| EP | 1 743 571 A2 | 1/2007 |
| JP | 58044078 | 3/1993 |
| JP | 08103568 | 4/1996 |
| WO | WO 96/05766 | 2/1996 |
| WO | WO 01/96986 A2 | 12/2001 |
| WO | WO 02/00111 | 1/2002 |
| WO | WO 02/078538 A2 | 10/2002 |
| WO | WO 03/015005 A2 | 2/2003 |
| WO | WO 2004/019172 A2 | 3/2004 |
| WO | WO 2004/032715 A2 | 4/2004 |
| WO | WO 2004/034221 A2 | 4/2004 |
| WO | WO 2005/016124 A2 | 2/2005 |
| WO | WO 2005/027720 A2 | 3/2005 |
| WO | WO 2005/029242 A2 | 3/2005 |
| WO | WO 2005/092177 | 10/2005 |

OTHER PUBLICATIONS

Busch, Fritz "Diabetes Institute Brings Dakota, New Ulm Together" Jun. 10, 2001. Ogden Newspapers, Inc.

Tibia.com website http://www.tibia.com!abouttibial?subtopic=whatistibia Apr. 27, 2007.

"Bluetooth." Wikipedia: The Free Encyclopedia. Aug. 10, 2009 <http://en.wikipedia.org/wiki/Bluetooth>.

Ichinoseki-sekine et al., "Improving the Accuracy of Pedometer Used by the Elderly with the FFT Algorithm," Medicine & Science in Sports & Exercise 2006,1674-1681.

Mann, W. et al., "Smart Phones for the Elders: Boosting the Intelligence of Smart Homes," Am. Assoc. for Artificial Intell., (AAAI), Jul. 2002.

Restriction Requirement of U.S. Appl. No. 11/768,167 dated Feb. 5, 2009.

Apr. 6, 2009 Response to Restriction Requirement of U.S. Appl. No. 11/768,167.

Notice of Non-Compliant Response of U.S. Appl. No. 11/768,167 dated May 6, 2009.

Jun. 8, 2009 Response to Notice of Non-Compliant Response of U.S. Appl. No. 11/768,167 dated May 6, 2009.

Office Action of U.S. Appl. No. 11/768,167 dated Aug. 19, 2009.

Dec. 21, 2009 Response to Office Action of U.S. Appl. No. 11/768,167 dated Aug. 19, 2009.

Final Office Action of U.S. Appl. No. 11/768,167 dated Mar. 24, 2010.

Jun. 24, 2010 Response to Final Office Action of U.S. Appl. No. 11/768,167 dated Mar. 24, 2010.

Advisory Action of U.S. Appl. No. 11/768,167 dated Jun. 30, 2010.

Office Action of U.S. Appl. No. 11/768,167 dated Dec. 27, 2010.

May 27, 2011 Response to Office Action of U.S. Appl. No. 11/768,167 dated Dec. 27, 2010.

Final Office Action of U.S. Appl. No. 11/768,167 dated Aug. 19, 2011.

Feb. 21, 2012 Response to Final Office Action of U.S. Appl. No. 11/768,167.

Final Office Action of U.S. Appl. No. 11/768,167 dated Sep. 7, 2012.

Examiner Interview Summary of U.S. Appl. No. 11/768,167 dated Jun. 13, 2013.

Amendment submitted with RCE of U.S. Appl. No. 11/768,167, filed Jun. 20, 2013.

Examiner Interview Summary of U.S. Appl. No. 11/768,167 dated Jun. 26, 2013.

Office Action of U.S. Appl. No. 11/768,167 dated Oct. 9, 2013.

Feb. 10, 2014 Reply to Oct. 9, 2013 Office Action of U.S. Appl. No. 11/768,167.

Examiner Interview Summary of U.S. Appl. No. 11/768,167 dated Jan. 27, 2014.

Examiner Interview Summary of U.S. Appl. No. 11/768,167 dated Feb. 6, 2014.

Final Office Action of U.S. Appl. No. 11/768,167 dated Mar. 10, 2014.

Examiner Interview Summary of U.S. Appl. No. 11/768,167 dated Mar. 18, 2014.

May 19, 2014 Reply to Final Office Action and After Final Consideration Pilot Program Request of U.S. Appl. No. 11/768,167.

Notice of Allowance of U.S. Appl. No. 11/768,167 dated Jun. 2, 2014.

Dugan et al., U.S. Appl. No. 14/297,123, titled: "Methods and Apparatus for Changing Mobile Telephone Operation Mode Based on Vehicle Operation Status," filed Jun. 5, 2014.

Dugan et al., U.S. Appl. No. 14/336,122, titled: "Methods and Apparatus for Controlling Appliances Using Biometric Parameters Measured Using a Wearable Monitor," filed Jul. 21, 2014.

Dugan et al., U.S. Appl. No. 14/467,036, titled: "Methods and Apparatus for Monitoring Stress Using Biometric Parameters Measured Using a Wearable Monitor," filed Aug. 24, 2014.

Restriction Requirement of U.S. Appl. No. 14/336,122 dated Oct. 8, 2015.

Supplemental Amendment of U.S. Appl. No. 14/336,122 filed Sep. 7, 2016.

Applicant-Initiated Interview Summary of U.S. Appl. No. 14/336,122 dated Sep. 8, 2016.

Oct. 13, 2016 Reply to Apr. 13, 2016 Non-Final Office Action of U.S. Appl. No. 14/467,036.

Aug. 15, 2016 Reply to Apr. 13, 2016 Non-Final Office Action of U.S. Appl. No. 14/336,122.

Mar. 8, 2016 Reply to Oct. 8, 2015 Restriction Requirement of U.S. Appl. No. 14/336,122.

Applicant-Initiated Interview Summary of U.S. Appl. No. 14/336,122 dated Mar. 16, 2016.

(56) References Cited

OTHER PUBLICATIONS

Non-Final Office Action of U.S. Appl. No. 14/336,122 dated Apr. 13, 2016.
Non-Final Office Action of U.S. Appl. No. 14/467,036 dated Apr. 13, 2016.
Interview Summary of U.S. Appl. No. 14/336,122 dated Apr. 18, 2016.
May 2, 2016 Reply to Oct. 30, 2015 Non-Final Office Action of U.S. Appl. No. 14/297,123.
Notice of Abandonment of U.S. Appl. No. 14/297,123 dated May 11, 2016.
Notice of Allowance and Examiner-Initiated Interview Summary of U.S. Appl. No. 14/297,123 dated Feb. 23, 2017.
Decision on Petition to Withdraw Abandonment of U.S. Appl. No. 14/297,123 dated Feb. 10, 2017.
Amendment Submitted with RCE of U.S. Appl. No. 14/336,122 filed Apr. 20, 2017.
Final Office Action of U.S. Appl. No. 14/336,122 dated Dec. 20, 2016.
Final Office Action of U.S. Appl. No. 14/467,036 dated Jan. 11, 2017.
Applicant-Initiated Interview Summary of U.S. Appl. No. 14/467,036 dated Jun. 19, 2017.
Non-Final Office Action of U.S. Appl. No. 14/336,122 dated Jul. 17, 2017.
Notice of Abandonment & Applicant-Initiated Interview Summary of U.S. Appl. No. 14/467,036 dated Jul. 21, 2017.
Applicant-Initiated Interview Summary of U.S. Appl. No. 14/336,122 dated Jul. 31, 2017.
Dec. 18, 2017 Reply to Jul. 17, 2017 Non-Final Office Action of U.S. Appl. No. 14/336,122.
Final Office Action of U.S. Appl. No. 14/336,122 dated May 3, 2018.

* cited by examiner

METHODS AND APPARATUS FOR ENCOURAGING WAKEFULNESS OF A DRIVER USING BIOMETRIC PARAMETERS MEASURED USING A WEARABLE MONITOR

This application is a continuation of and claims priority to U.S. patent application Ser. No. 14/297,123 filed Jun. 5, 2014, and entitled "METHODS AND APPARATUS FOR CHANGING MOBILE TELEPHONE OPERATION MODE BASED ON VEHICLE OPERATION STATUS", which is a continuation of and claims priority to U.S. patent application Ser. No. 11/768,167 filed Jun. 25, 2007, now U.S. Pat. No. 8,781,568, and entitled "SYSTEMS AND METHODS FOR HEART RATE MONITORING, DATA TRANSMISSION, AND USE", which claims priority to U.S. Provisional Patent Application Ser. No. 60/805,726 filed Jun. 23, 2006 and entitled "SYSTEMS AND METHODS FOR HEART RATE MONITORING, DATA TRANSMISSION, AND USE", and U.S. Provisional Patent Application Ser. No. 60/805,838, filed Jun. 26, 2006 and entitled "SYSTEMS AND METHODS FOR HEART RATE MONITORING, DATA TRANSMISSION, AND USE". Each of the above applications is hereby incorporated herein by reference in its entirety for all purposes.

FIELD OF THE INVENTION

The present invention relates to use of feedback from heart rate monitors, and more particularly to systems and methods for heart rate monitoring, data transmission, and use.

BACKGROUND

Portable heart rate (HR) monitoring devices are commonly used in fitness related activities for weight loss, goal HR training, and general HR monitoring. Additionally, HR monitors (HRMS) may sometimes be employed by healthcare professionals for chronic and/or acute heart condition monitoring and/or diagnosis. Some HRMS include a chest strap which senses, receives and/or detects signals from a user's heart.

Portable HR monitoring devices typically are expensive, and in some cases are cost prohibitive for many consumers. A need exists for inexpensive and/or simplified HR monitoring systems.

SUMMARY OF THE INVENTION

In a first aspect of the invention, a heart rate monitoring system is provided that includes (1) a heart rate monitor adapted to wirelessly transmit a signal indicative of a heart rate of a user; and (2) a user device adapted to receive the signal from the heart rate monitor, process the signal, and determine sleep information for the user from the heart rate.

In a second aspect of the invention, a method of monitoring a driver is provided that includes (1) determining a heart rate of the driver; (2) determining whether the driver's heart rate is within a predetermined range; (3) prompting driver feedback if the driver's heart rate is not within the predetermined range; and (4) determining if driver feedback is received.

In a third aspect of the invention, a method of reducing functionality of a cellular telephone is provided that includes (1) determining if a vehicle is parked; and (2) if the vehicle is not parked, sending a restricting signal to the cellular telephone that restricts which calls may be made or received by the cellular telephone. Numerous other aspects are provided.

Other features and aspects of the present invention will become more fully apparent from the following detailed description, the appended claims and the accompanying drawings.

DETAILED DESCRIPTION OF THE INVENTION

Portable heart rate (HR) monitoring devices are commonly used in fitness related activities for weight loss, goal HR training, and general HR monitoring. Additionally, HR monitors (HRMS) may sometimes be employed by healthcare professionals for chronic and/or acute heart condition monitoring and/or diagnosis. Some HRMS include a chest and/or wrist strap which senses, receives and/or detects signals from or motion of a user's heart and transmits a representative signal to a receiver which displays and/or records the user's HR.

In at least one embodiment of the invention, a HRM is modified to incorporate Bluetooth™ or a similar technology. The HRM may be "paired" with any of a number of devices such as a PDA, cellular telephone or the like. For example, an existing HRM may be modified to include a Bluetooth™ transmitter and/or may be retrofitted by attachment of a Bluetooth™ transmitter external to the HRM. Additionally, a HRM may be constructed with a Bluetooth™ or similar transmitter incorporated into a wrist strap, a chest strap, or the like. Similarly, other short-range, low-power communications technologies and other communications transmission formats may be employed.

Bluetooth™ Heart Rate Monitoring

Figure 1:
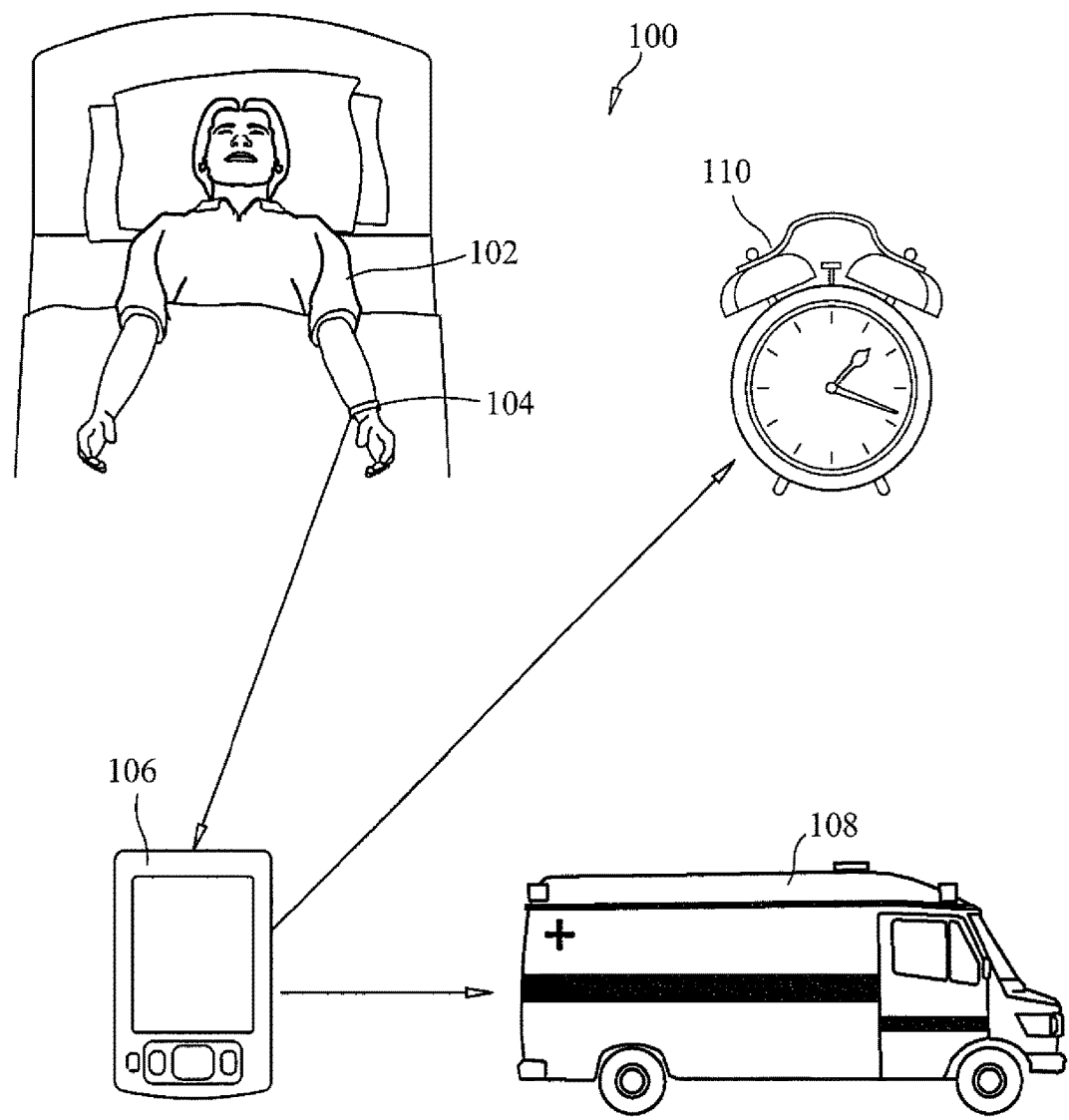
FIG. 1 is a schematic view of a wireless network in accordance with some aspects of the invention.

According to some embodiments of the present invention, use of a Bluetooth™ enabled HRM in an interactive network 100 is shown in FIG. 1. The network 100 may include a user 102, who may wear a Bluetooth™ enabled HRM 104 (e.g., a chest strap, a wrist strap, etc.). The HRM 104 is capable of wirelessly transmitting a signal to a user device 106 (e.g., a personal digital assistant (PDA), a cellular telephone, a laptop or personal computer, or the like).

In some embodiments, the user device 106 may be capable of transmitting a signal (based on the signal received from the HRM 104) to an interested party 108 such as a doctor, an emergency medical service, a police or fire department, an insurance company or the like. Additionally, the user device 106 may also be capable of transmitting a signal to an alarm system 110 or may itself generate an alarm (as described below). In the same or alternative embodiments, the HRM 104 may be capable of transmitting signals directly to the interested party 108 and/or alarm system 110. Other devices and/or parties may be included in or operatively coupled to the network 100 (e.g., room lighting, tracking software, personal computers, etc.).

In one or more embodiments, the HRM 104 may be any Bluetooth™ enabled HRM as discussed generally above. Other communications protocols and/or systems may alternatively or additionally be used.

User device 106 may be any device that is capable of supporting Bluetooth™ or similar technology. For example, the user device may be a cellular telephone, a web-enabled device such as a web-enabled cellular telephone or PDA, a portable web browser, a cellular or web-enabled wrist watch, a headset, ear piece, a microphone, a speaker, alarm clock, web-enabled or otherwise portable gaming device, a portable or desk top computer, an automobile, or any other suitable device. In some embodiments, the user device 106 may be capable of receiving, transmitting, storing, compiling, logging, tabulating, and/or analyzing HR and/or health-related information received from HRM 104.

The interested party 108 may be any person or entity to be alerted of a condition of the user 102. For example, the interested party 108 may be a parent, caretaker, family member, doctor, nurse, emergency service (e.g., 911), insurance company or the like and/or the user 102. In some embodiments, the interested party 108 may be a personal computer, Web server, tracking network, etc. Such embodiments may be employed, for example, for research, information logging, and/or when the user 102 is not expected to require immediate assistance.

The alarm system 110 may be a conventional alarm type clock which is Bluetooth™ or otherwise wirelessly enabled. Alternatively, the alarm system 110 may be part of the user device 106, a cell phone, a PDA, a computer, etc. As with the HRM 104, the alarm system 110 may be a current commercially available product modified for use in the present system or may be a new device designed and constructed for use in the network 100. The alarm system 110 may include an alarm clock, lighting adjusters (e.g., dimmers), audio output (e.g., radio or CD player), and/or other devices which may be used for waking up the user 102. The alarm 110 may be further adapted to monitor, analyze and/or record information received from the HRM 104 and/or the user device 106. In some embodiments, the alarm system 110 may not include a clock.

In operation, it may be desirable to track the HR of a user 102 during sleep and/or other periods of reduced activity. For example, it may be desirable to monitor the HR of an infant, elderly person, person with a heart condition, or someone who may be prone to sleep apnea or any cardio/pulmonary disorder or condition. This may be especially useful during sleep or when a caretaker cannot be with the user 102.

In some embodiments, the HRM 104 may send a signal indicative of the user 102's HR to the user device 106 continuously, intermittently, or at a predetermined interval. In other embodiments, the HRM 104 may only send a signal to the user device 106 when the HR of the user 102 detected by the HRM 104 drops below a certain predetermined level (or exceeds a predetermined level).

When a low, inconsistent, or no HR signal is received at the user device 106, the wireless device 106 may initiate contact with the interested party 108. In one example, this may be employed when a user 102 with a heart condition lives alone. When the HRM 104 determines there is no, an inconsistent, or a low HR, the HRM 104 may send a signal to the user device 106 (e.g., a cellular phone) which calls/dials 911. The user device 106 may be equipped to transmit a prerecorded message to a 911 dispatcher or another interested party (e.g., including the identity of the user 102, the location of the user 102, medical, current condition and/or history information about the user 102, etc.). Additionally or alternatively, the user device 106 may transmit HR information to the 911 dispatcher or another interested party. The above information may be transmitted to any relevant party (e.g., a caregiver, a doctor, family member, a nurse, a fire department, a police department, etc.).

In another example, the HRM 104 may be worn by an infant user 102. When a HR signal is detected that indicates a HR below a threshold value, the HRM 104 and/or the user device 106 may transmit an alarm signal to a parent in another room and/or may transmit an alarm signal to activate an alarm system 110 to alert the parent. For example, the alarm signal may be transmitted to a PDA, a cellular telephone, a land line, a home or other alarm system, etc.

The network 100 may also be employed to monitor sleep patterns for research, for fitness tracking, for health concerns, to enable chronobiologic sleep, or for other similar reasons. For example, to facilitate chronobiologic sleep, the HRM 104 may transmit HR information to the user device 106 continuously or at predetermined intervals. The user device 106 may receive the HR information and generate an alarm (e.g., at the user device 106 and/or by sending a signal to the alarm system 110) when a predetermined HR level or series of levels is achieved. For example, a user 102 may plan to sleep for a certain number of sleep cycles (e.g., for approximately a certain amount of time). Progressing through a sleep cycle may be detected by changes in HR monitored by the HRM 104. When the user device 106 receives HR information from the HRM 104, it may analyze and/or process the HR information to determine the stage of sleep. When the appropriate HR is reached (e.g., the proper point in the sleep cycle), the user device 106 may wake the user 102 (e.g., such as by generating an alarm, sending a signal to the alarm 110, etc.). For example, the alarm 110 may be a dimmer attached to a bedside lamp. The dimmer may slowly brighten the lamp to correspond to the sleep cycle (e.g., HR) and wake the user 102. In the same or other embodiments, audio feedback may be used. In some embodiments, sound and/or light may be adjusted to induce and/or maintain sleep. For instance, if the measured HR exceeds the expected HR for a certain stage in the sleep cycle, the user device 106 may send a signal to the alarm 110 and cause the alarm 110 (e.g., a radio) to play low and soothing music to ease the user 102 back into sleep. Alternatively, the user device 106 may directly play low and/or soothing music (e.g., in an MP3 player embodiment of the user device 106). Also, the level of sound and/or light may be adjusted to correspond to HR as the user 102 falls asleep, thus acting to help cause sleep and/or also serving as a timer to turn off unused appliances.

In at least one embodiment of the invention, the sleep patterns of the user 102 may be monitored using the HRM 104. For example, the HRM 104 may measure the HR of the user 102 each evening when the user 102 sleeps. HR information may be communicated from the HRM 104 to the user device 106 (or any other device), compiled and/or analyzed to determine how restful or complete each evenings sleep was. Variables such as room temperature, clothing worn by the user, type or number of blankets or sheets employed, dietary habits, etc., may be stored, analyzed and/or correlated with sleep. Sleep patterns may be compared for different nights of a week, month, etc. Additionally, conditions such as sleep apnea, reflux, seizures, etc., may be identified (e.g., based on hear rate variations).

In some embodiments, the user device 106 may track sleep or sleep deprivation, and provide feedback to the user 102 regarding how best to improve or obtain the optimal amount of sleep. For example, if the user device 106 is a PDA, cellular phone or similar device, the user device 106 may automatically remind the user to start getting ready for bed earlier in the evening (e.g., via a calendar or alarm).

In the same or other embodiments, the user device 106 may monitor the stress level of the user 102 (e.g., based on HR). For example, if the HR of the user 102 exceeds a predetermined threshold, the user device 106 may sound an alarm, or otherwise notify the user 102 of the condition. The user device 106 may attempt to calm the user 102 (e.g., by playing relaxing music, playing a pre-recorded relaxing message, etc.). In some embodiments, a graph of HR may be displayed on the user device 106. For instance, current HR may be displayed relative to an "ideal" HR for the user 102 so that the user 102 may visually observe his/her stress level.

In one particular embodiment, the user device 106 may be a cellular telephone or PDA that monitors the stress level of the user 102 (e.g., daily). The user device 106 may identify "patterns" of stress, such as certain times of the day or activities that appear to cause the user 102 stress. In this manner, the user 102 may be able to break cycles of stress and/or choose less stressful activities during historically stressful time periods.

In some embodiments, the HR patterns of two or more people may be compared and/or analyzed. For example, a user 102 may provide HR pattern information (e.g., recorded by the user device 106) to the user device of another person. In one exemplary embodiment, the HR patterns of a husband/wife, girlfriend/boyfriend, parent/child, etc., may be monitored during a discussion or therapy session and used as an aid to identify what topics, situations and/or the like create stress or agitation in each party.

Likewise, HR patterns may be used to determine compatibility between people. For example, a Web-based dating cite may compare typical or exemplary HR patterns of potential dating candidates, such as during similar situations and/or experiences, to determine compatibility (e.g., "low" stress candidates may be compatible, as may be "high" stress candidates). Likewise, an employer may wish to assign employees to a working group with similar HR patterns/stress levels, or provide a mix of high and low stress employees.

In some embodiments, the HRM 104 may be paired with a user device 106 such as for example, a clock radio or wireless phone. The HRM 104 may include a controller (not shown) adapted to detect a medical condition or medical event/episode (e.g., a heartbeat pattern indicative of failure to breathe associated with sleep apnea, choking, heart attack, seizure, intoxication, etc.) In response to detecting such a pattern, the controller in the HRM 104 may send a signal to the user device 106 to, for example, wake the user 102 or a caregiver. For example, using sound, light, electric shock, etc. The controller may record such medical events/episodes so that a medical condition may be diagnosed and/or treated. In some embodiments, the user device 106 may include the controller or an additional controller adapted to identify the medical event HR pattern. In addition, other types of monitors (e.g., breathing monitors, body/chest motion sensors, urine or moisture sensors, body position sensors, blood flow sensors, temperature sensors, etc.) may be used to identify patterns associated with medical and other events/episodes. For example, an HR pattern detected by the HRM 104 and a chest motion pattern detected by a chest motion sensor that individually or together indicate the user 102 is asleep and not breathing may be used by the controller to identify a sleep apnea episode. Once the sleep apnea episode is identified, the controller may initiate attempts to wake the user 102, for example, by playing loud music or shocking the user 102 via the user device 106 or with a small electric charge administered via contacts, e.g., on the HRM 104. The controller may continue attempts to wake the user 102 until an HR pattern corresponding to an awake condition is detected. In some embodiments, the attempts to wake may escalate in terms of severity (e.g. louder volume, brighter light, higher voltage shocks) until an awake/breathing condition is detected.

HR Use in Vehicles

First Exemplary Embodiment

It may be desirable to monitor the HR of a vehicle driver. Similar to HR monitoring during sleep as described above, a Bluetooth™ enabled or similar HR monitor may be used to encourage or help maintain wakefulness while driving. This may be useful for those with heart conditions, driving at night, and/or for long-haul drivers such as truck drivers.

Figure 2A:
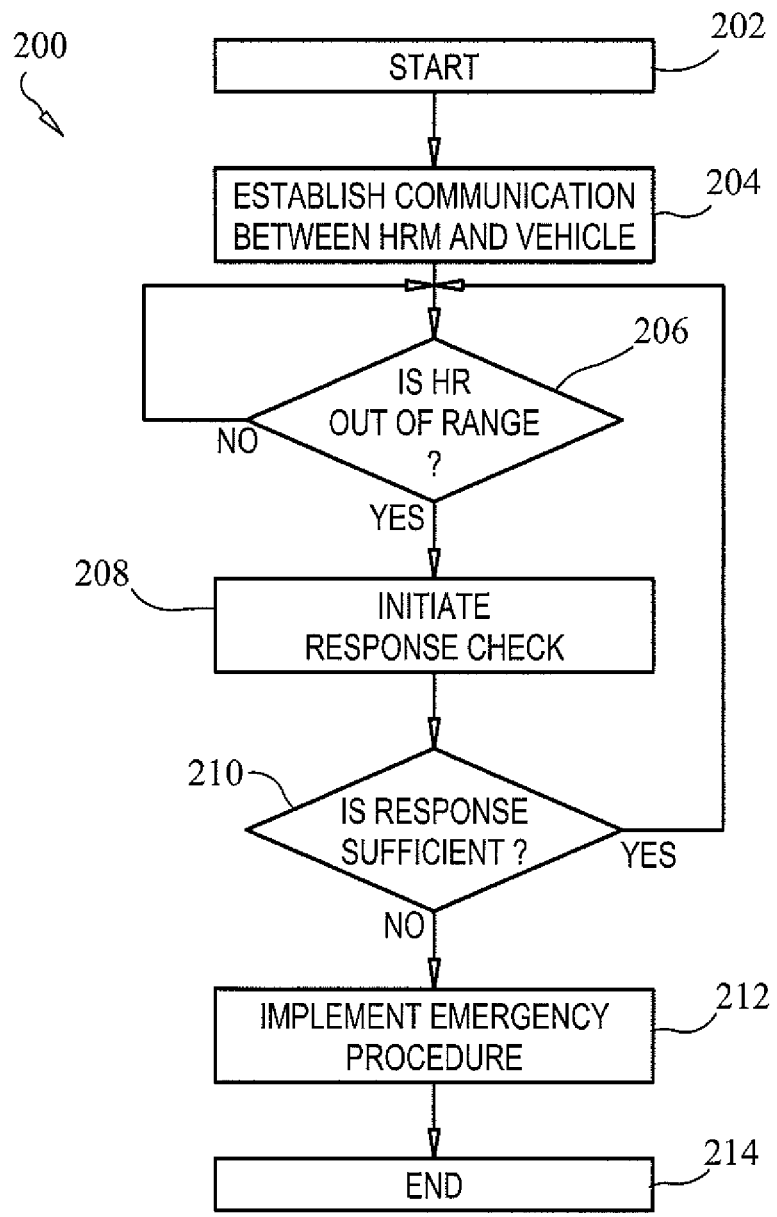
FIG. 2A is a flow diagram of a method of monitoring a driver's response in a vehicle with a wireless device in accordance with some aspects of the invention.

FIG. 2A is a flow diagram of a method 200 of monitoring a driver's response in a vehicle with a HR monitor such as a Bluetooth™ enabled HR monitor. The method 200 may be employed, for example, in Bluetooth™ enabled vehicles, such as certain Acura models manufactured by American Honda Motor Co. Inc. of Torrance, Calif., or by using a retrofit system, such as UConnect available from Daimler-Chrysler Corporation of Auburn Hills, Mich. These systems may enable communication between the user's wireless HRM and the vehicle via Bluetooth™ or other wireless protocols (although a hardwired system also may be used). Alternatively, the HRM may communicate with another device (e.g., a cellular phone, a PDA, a portable web browser, etc.) that may or may not in turn communicate with the vehicle.

The method 200 starts at step 202. In step 204, the HRM initiates communication with the vehicle (e.g., establishes a Bluetooth™ connection) either directly or through another device (e.g., a cellular telephone, a PDA, etc.).

In step 206, the HRM checks the driver's HR. If the driver's HR is within an acceptable range for the driver, the method returns to step 206 to recheck the driver's HR. A driver's HR may be checked continuously, randomly or at any predetermined interval. Too low of a HR may indicate that the driver is about to fall asleep or is too relaxed to respond to current driving conditions (e.g., bad weather such as rain, snow sleet, etc.). Likewise, too high of a HR may indicate that the driver is too stressed to respond to current driving conditions (e.g., bad weather such as rain, snow, sleet, etc., stressful situations such as crowded driving, a traffic jam, etc.). A high stress level (e.g., rapid heart rate) may indicate that the driver is experiencing anxiety, road rage, etc., and as described below, the vehicle or another device may attempt to calm the driver down with pre-recorded messages, relaxing music, chants, spiritual quotations, etc. Similarly, when the driver's HR is too low, the vehicle or another device may attempt to rouse the driver into a more wakeful state (e.g., by playing load music, honking the car's horn, etc). In extreme stress or low HR situations, another party may be notified (e.g., a family member, the police, etc., such as via a cellular telephone) or the vehicle may take corrective action (e.g., braking, slowing down, stopping, limiting acceleration or speed, etc.).

The acceptable range of the driver's HR may be determined based on various additional factors for example, the time of day, traffic or weather conditions, current road speed, drive time, driver experience, driver health, driver weight, body mass index, age, medical history, etc.

In some embodiments, the driver's HR is checked more frequently as it approaches the upper and lower limits of an acceptable HR range. As stated, an acceptable HR range may include, in some embodiments, a lower range which is indicative of a relaxed wakefulness state (e.g., a near sleep condition). Entry into this lower range may initiate a response check in step 208. Also, if the HR is outside of the acceptable range for the driver, a warning, alarm or the like may be sounded to alert the driver or another interested party (as described below).

In step 208, a response check is initiated. For example, the vehicle may prompt the driver (e.g., via a voice command issued through the vehicle's stereo or navigation system) to respond in a manner that indicates the alertness level of the driver. In some embodiments, the driver may be directed to adjust radio volume, verbally reply, sing a song, turn on a turn signal, flash the vehicle's headlights, depress a series of buttons on a control panel, and/or any other appropriate action. In one or more embodiments, the driver's response may be timed to determine if the driver is sufficiently alert. (Note that an appropriate level of alertness may vary based on driving conditions, time of day, etc.). In some embodiments, the response check may cause the vehicle's stereo volume to increase significantly and/or cause the vehicle's horn to sound (e.g., to ensure that the driver is alert enough to participate in the response check). The driver's HR may then be rechecked to determine if the auditory stimulus was sufficient, and the auditory or other stimulus repeated if necessary.

In step 210, the driver's response is checked. If the driver's response indicates alertness, the method passes back to step 206, where monitoring of the driver's HR resumes. In some embodiments, monitoring resumes at a more frequent rate after a response check has been initiated. (Note that in some embodiments, a driver's response may be checked at predetermined intervals without regard for HR.) If the driver's response is not sufficient in step 210, the method passes to step 212.

In step 212, when an insufficiency is determined in the driver's response at step 210, an emergency procedure may be implemented. For example, a family member and/or an emergency service such the police and/or fire department may be contacted (e.g., via a cellular telephone or other communications service including, for example, using a vehicle's on-board communication system, such as OnStar™ by GM, manufactured by OnStar of Detroit, Mich.). In some embodiments, the emergency procedure may include turning on some or all lights in the vehicle, sounding the vehicle's horn, turning up the volume of the vehicle's stereo, turning on the vehicle's hazard signals, slowing the vehicle down, etc.).

The method ends at step 214.

Second Exemplary Embodiment

Similar to HR monitoring during sleep as described above, a Bluetooth™ enabled or similar HR monitor may be used to encourage wakefulness while driving via use of a wireless device (e.g., a cellular telephone, PDA, MP3 player or the like). This may be useful for those with heart conditions, driving at night, and/or for long-haul drivers such as truck drivers.

Figure 2B:
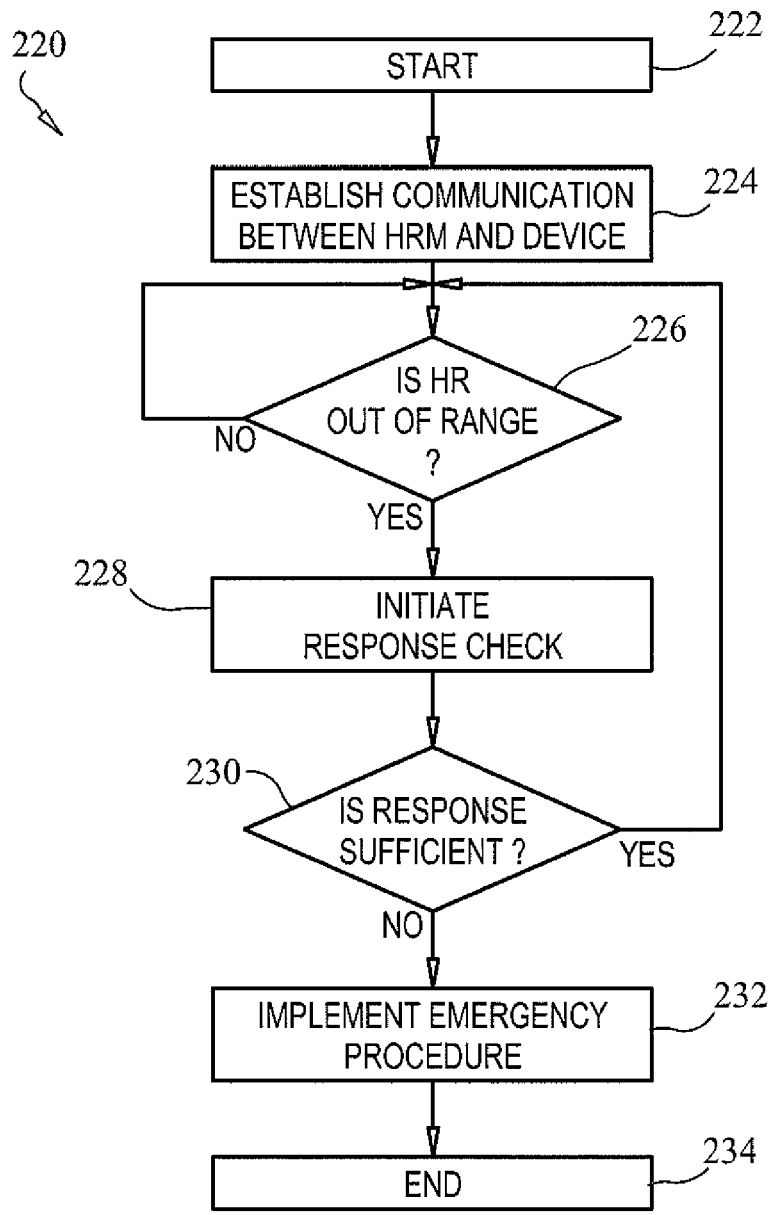
FIG. 2B is a flow diagram of a method of encouraging wakefulness in accordance with the present invention.

FIG. 2B is a flow diagram of a method 220 of encouraging wakefulness in accordance with the present invention. The method 220 may be employed, for example, to encourage wakefulness in a vehicle such as a truck, car, airplane, etc., or whenever a person wants to remain awake. For convenience, the method 220 is described with reference to a driver, although a similar method may be used to encourage wakefulness of any person in any venue.

The method 220 starts at step 222. In step 224, the wireless HRM initiates communication (e.g., establishes a Bluetooth™ connection) with a user device (e.g., a cellular telephone, a PDA, an MP3 player, etc.).

In step 226, the HRM and/or user device checks the driver's HR. If the driver's HR is within an acceptable range for the driver, the method returns to step 226 to recheck the driver's HR. A driver's HR may be checked continuously, randomly or at any predetermined interval. Too low of a HR may indicate that the driver is about to fall asleep or is too relaxed to respond to current driving conditions (e.g., bad weather such as rain, snow sleet, etc.). Likewise, too high of a HR may indicate that the driver is too stressed to respond to current driving conditions (e.g., bad weather such as rain, snow, sleet, etc., stressful situations such as crowded driving, a traffic jam, etc.). A high stress level (e.g., rapid heart rate) may indicate that the driver is experiencing anxiety, road rage, etc., and as described below, the user device (and/or the vehicle) may attempt to calm the driver down with pre-recorded messages, relaxing music, chants, spiritual quotations, etc. Similarly, when the driver's HR is too low, the user device (and/or the vehicle) may attempt to rouse the driver into a more wakeful state (e.g., by ringing, playing load music, honking the car's horn, or making another audible sound, by vibrating, etc). In extreme stress or low HR situations, another party may be notified (e.g., a family member, the police, etc., such as via a cellular telephone) or the vehicle may take corrective action (e.g., braking, slowing down, stopping, limiting acceleration, etc.).

In some embodiments, the driver's HR is checked more frequently as it approaches the upper and lower limits of an acceptable HR range. As stated, an acceptable HR range may include, in some embodiments, a lower range which is indicative of a relaxed wakefulness state (e.g., a near sleep condition). Entry into this lower range may initiate a response check in step 228. Also, if the HR is outside of the acceptable range for the driver, a warning, alarm or the like may be sounded to alert the driver or another interested party (as described below).

In step 228, a response check is initiated. For example, the user device (and/or the vehicle) may prompt the driver to respond in a manner that indicates the alertness level of the driver. In some embodiments, the driver may be directed to press a button on the user device, adjust user device and/or vehicle radio volume, verbally reply, turn on a turn signal, flash the vehicle's headlights, depress a series of buttons on the user device and/or a control panel of the vehicle, and/or any other appropriate action. In one or more embodiments, the driver's response may be timed to determine if the driver is sufficiently alert. (Note that an appropriate level of alertness may vary based on driving conditions, time of day, etc.). In some embodiments, the response check may cause the user device's volume (e.g., an MP3 player, cellular telephone, etc.) or vehicle's stereo volume to increase significantly and/or cause the user device to sound an alarm and/or the vehicle's horn to sound (e.g., to ensure that the driver is alert enough to participate in the response check). The driver's HR may then be rechecked to determine if the auditory stimulus was sufficient, and the auditory or other stimulus repeated if necessary.

In step 230, the driver's response is checked. If the driver's response indicates alertness (or a not-to-stressed level), the method passes back to step 226, where monitoring of the driver's HR resumes. In some embodiments, monitoring resumes at a more frequent rate after a response check has been initiated. (Note that in some embodiments, a driver's response may be checked at predetermined intervals without regard for HR.) If the driver's response is not sufficient, the method passes to step 232.

In step 232, when an insufficiency is determined in the driver's response at step 230, an emergency procedure may be implemented. For example, a family member and/or an emergency service such the police and/or fire department may be contacted (e.g., via a cellular telephone or other communications service including, for example, using a vehicle's on-board communication system, such as OnStar™ by GM, manufactured by OnStar of Detroit, Mich.). In some embodiments, the emergency procedure may include turning up the volume of the user device (e.g., in an MP3 player, cellular telephone or similar embodiment), sounding an audible alarm, turning on some or all lights in the vehicle, sounding the vehicle's horn, turning up the volume of the vehicle's stereo, turning on the vehicle's hazard signals, slowing the vehicle down, etc.

The method ends at step 234.

Figure 2C:
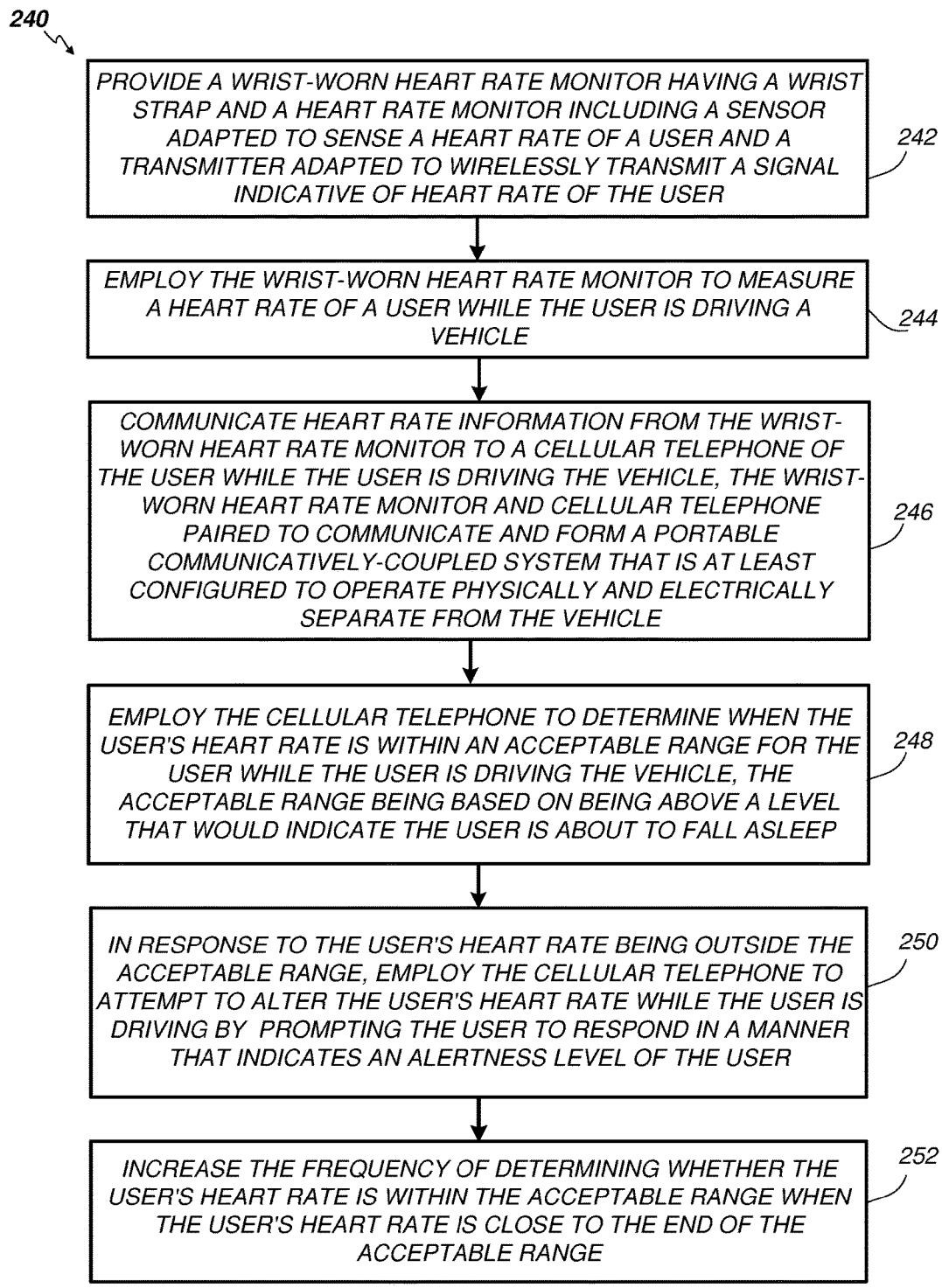
FIG. 2C is a flow diagram of a method of encouraging wakefulness in accordance with the present invention.

FIG. 2C is a flow diagram of a method 240 of encouraging wakefulness in accordance with the present invention. The method 240 of maintaining wakefulness of a driver of a vehicle using a cellular telephone and a wrist-worn heart rate monitor includes providing a wrist-worn heart rate monitor having a wrist strap and a heart rate monitor including a sensor adapted to sense a heart rate of a user and a transmitter adapted to wirelessly transmit a signal indicative of heart rate of the user (242). The method 240 also includes employing the wrist-worn heart rate monitor to measure a heart rate of a user while the user is driving a vehicle (244). Next, heart rate information is communicated from the wrist-worn heart rate monitor to a cellular telephone of the user while the user is driving the vehicle, the wrist-worn heart rate monitor and cellular telephone paired to communicate and form a portable communicatively-coupled system that is at least configured to operate physically and electrically separate from the vehicle (246). Then the cellular telephone can be employed to determine when the user's heart rate is within an acceptable range for the user while the user is driving the vehicle, the acceptable range being based on being above a level that would indicate the user is about to fall asleep (248). In response to the user's heart rate being outside the acceptable range, the cellular telephone is employed to attempt to alter the user's heart rate while the user is driving by instructing the user to perform an activity specifically-selected so as to alter the user's wakefulness or by prompting the user to respond in a manner that indicates an alertness level of the user (250). The frequency of determining whether the user's heart rate is within the acceptable range is increased when the user's heart rate is close to an end of the acceptable range (252).

Restricting Device Use

Certain electronic devices, such as Bluetooth™ enabled cellular telephones, may interact with a vehicle and/or may be integrated with a vehicle system. For example, a Bluetooth™ cellular telephone may communicate with some vehicles to create a hands-free telephone (e.g., through use of the vehicle's audio system). In some vehicles, a user may operate the cellular telephone via voice commands and/or by pushing certain buttons on a vehicle's steering wheel and/or dashboard. These systems may improve the ability of a driver to concentrate on road conditions, but do not entirely eliminate distractions associated with cellular telephones (e.g., dialing numbers, hanging up a call, answering a call, checking voice mail messages, etc). The distraction of cellular telephone use, even in hands-free versions, may significantly reduce the ability of a driver to safely operate a vehicle, especially in the case of inexperienced drivers.

Figure 3:
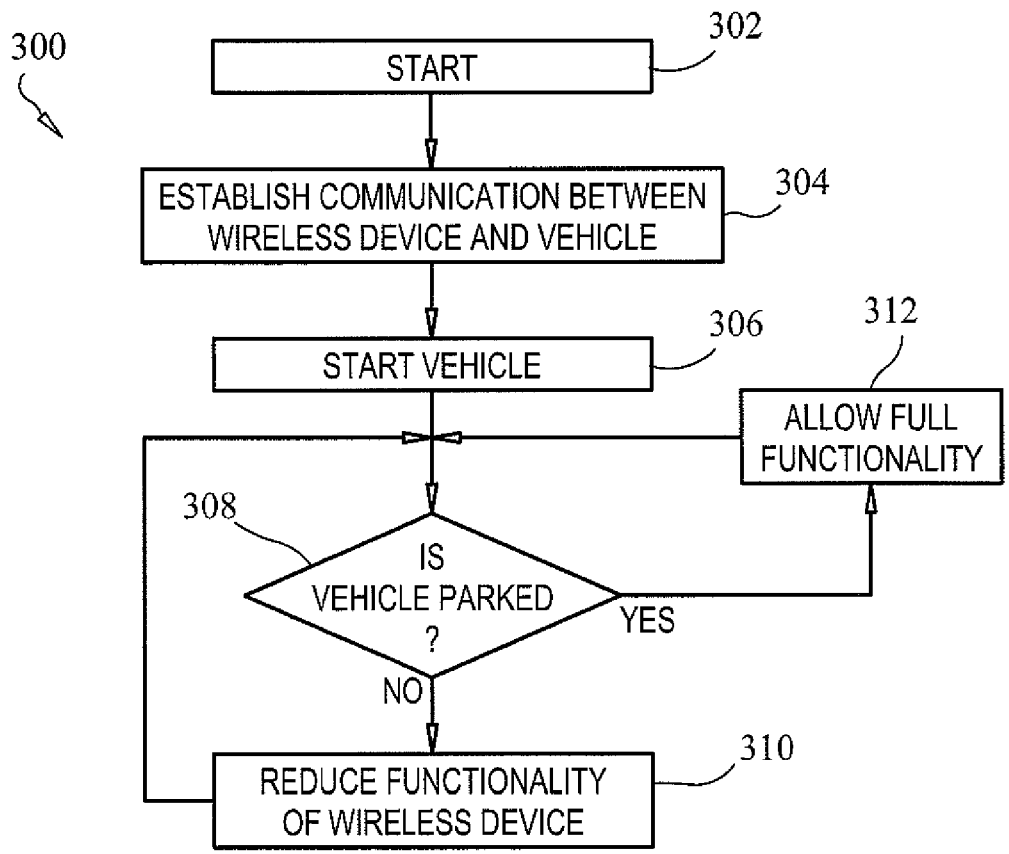
FIG. 3 is a flow diagram of a method of restricting use of a wireless device in a vehicle in accordance with some aspects of the invention.

FIG. 3 is a flow diagram of a method of restricting use of a wireless device, such as a cellular telephone, in a vehicle. The method begins at step 302.

In step 304, a user of a wireless device, such as a cellular telephone, approaches and/or enters a vehicle. Assuming the wireless device and the vehicle are powered on, communication between the wireless device and vehicle is established and/or enabled. For example, a wireless communication channel may be established between the wireless device and the vehicle, such as a Bluetooth™ connection and/or a Bluetooth™ pairing. In many cases, the wireless device (e.g., cellular telephone) may be on as the driver enters the vehicle, and establishment of communication between the wireless device and vehicle may occur automatically. In some cases, the engine of the vehicle need not be running to establish communication between the wireless device and vehicle (e.g., if the audio and/or other systems of the vehicle have power).

Note that the vehicle may establish contact with the wireless device by having the vehicle issue a signal to all wireless devices in its proximity. In some embodiments, the vehicle may scan and detect certain wireless devices (e.g., the devices of certain drivers) and/or may be encoded to communicate only with specific wireless devices.

In step 306, the driver starts the vehicle if it is not already running.

After the vehicle establishes contact with the wireless device and/or is running, in step 308, a check is performed to determine if the vehicle is parked (e.g., in park, in neutral, not moving, etc.). In some embodiments, the wireless device operates normally (e.g., with full call in/call out, web browsing, etc., functionality) when the vehicle is parked or otherwise stationary. For example, full functionality of the wireless device may only be enabled when the vehicle is parked or stationary (as described below). The parked or stationary status of the vehicle may be continuously, periodically or randomly monitored to determine whether the vehicle is in motion.

Assuming the vehicle is shifted out of park or neutral or otherwise engaged for motion, the method 300 proceeds to step 310. In step 310, functionality of the wireless device is limited. For example, the vehicle may issue a restricting signal to the wireless device. The restricting signal may cause the wireless device to operate in a restricted mode while the vehicle is moving, shifted out of park or neutral, etc. When the wireless device is a cellular telephone, in some embodiments, the restricted mode of operation for the wireless device will not allow any incoming or outgoing calls. In other embodiments, certain telephone calls may be placed and/or received while in a restricted mode of operation. For example, a cellular telephone may be allowed to call only certain telephone numbers such as emergency services numbers (e.g., 911), parent or guardian numbers, etc. In one exemplary embodiment, a parent or other interested party may program which telephone numbers are acceptable for a driver to call or be called by (e.g., so as to prevent a teenage driver from using the wireless device while driving, except for emergencies). Such programming may be performed using features of the vehicle (e.g., via a user interface such as a navigation screen) and/or by using features of the wireless device.

After the wireless device is switched into a restricted mode of operation (step 310), the "parked" status of the vehicle may be monitored (step 308) to determine if the vehicle has stopped, been parked, etc. While the vehicle is in motion, the wireless device may remain in a restricted mode of operation. In some embodiments, once the vehicle is stopped and/or parked, the vehicle may issue a releasing signal (step 312) that returns the wireless device to full functionality (or to an increased level of functionality). The method may then proceed to step 308 to recheck the "parked" status of the vehicle.

In at least one embodiment, it may be desirable to allow a driver or passenger to override the restricted mode of operation of a wireless device. For example, in an emergency, even while a vehicle is in motion, it may be necessary for a driver or passenger to place a telephone call. In some embodiments, such an "override" condition may be communicated automatically to a third party (e.g., parent, an emergency service, etc.)

Cellular telephone access may be similarly limited on subways or airplanes, in hospitals, movie theaters, restaurants, etc., through use of "restricting" signals that place a cellular telephone in a restricted mode of operation (e.g., allow calls only to emergency services, for example). In the case of Bluetooth™, the process of limiting wireless device functionality may be referred to as "Bluetooth™ disabling", or the wireless device may said to be "Bluetooth™ disabled".

The functionality of other wireless devices may be similarly limited. For example, use of a laptop computer, portable music player (e.g., MP3), portable gaming device, etc. may be similarly limited or prohibited in certain venues (e.g., airplanes, airports, hospitals, etc.).

One technique for implementing restricted calling in a vehicle is to associate a restricted call list with the vehicle. For example, if the vehicle is adapted to allow hands free communication with a cellular telephone, the vehicle may be programmed with a list of "acceptable" telephone numbers, and only calls placed to or received by those telephone numbers will be routed through the vehicle (e.g., the vehicle's audio system). However, such an implementation may not prevent a user from simply using a cellular telephone without the vehicle's audio system, and requires programming of every relevant vehicle. In another embodiment, a cellular phone is programmed to operate in a restricted mode upon receipt of one or more signals from a vehicle (as described above). Such an embodiment allows multiple vehicles to initiate the restricted mode of operation, as well as other venues (e.g., hospitals, restaurants, airplanes, etc.).

The foregoing description discloses only exemplary embodiments of the invention; modifications of the above disclosed apparatus and methods which fall within the scope of the invention will be readily apparent to those of ordinary skill in the art. For instance, although discussed primarily with regard to Bluetooth™ technology, it is understood that signals may be sent to and from the HRM, wireless device, and/or other devices via other means, such as Short Message Service, IEEE 802.11b (WiFi), Ultra Wide Band (UWB), WiMax, etc.

Additionally, while the present invention has primarily been described with reference to a single user, it will be understood that the invention is equally applicable to multiple user situations. For instance, a nurse or home health care provider may serve as an interested party to multiple users, such as in a nursing home. In this way, multiple users may connect multiple HR monitors to either collective or individual wireless devices which may relay information to the nurse or other interested party.

In some embodiments, a HRM may communicate HR information to a portable music player, such as an MP3 player. For example, a HRM may wirelessly transmit data to an iPod available from Apple Computer, Inc. of Cupertino, Calif. The MP3 player may be programmed to perform any of the above described methods, including assisting a user in monitoring, analyzing and/or improving sleep (e.g., by playing relaxing music at appropriate times and/or sleep cycles). Such a device may be referred to as an "iNod".

As stated, in some embodiments, HR monitoring may be used to encourage sleep or encourage wakefulness. In at least one embodiment, a cellular telephone, a PDA, an MP3 player or the like may receiving a HR signal (wirelessly or through a hardwired connection), and encourage either sleep or wakefulness by employing the HR signal. Such a device and/or method may be, for example, referred to as "Nodsense". A cellular telephone, PDA, MP3 player, etc., may (e.g., be programmed to) operate in both modes. For example, a user may employ an MP3 player while in bed to monitor HR and encourage sleep, and employ the MP3 player while in a vehicle to monitor HR and encourage wakefulness. A cellular telephone, PDA, etc., may be similarly employed. Likewise, these device may be further configured to (e.g., programmed to) monitor stress levels (as previously described), and/or to count calories taken in and/or burned during a day.

A cellular phone hardwired to a vehicle may be also disabled (as described above).

In some embodiments, the HRs of employees may be monitored (e.g., via company supplied PDAs, cellular phones, etc., using wireless or other HRMS). Stress level, sleepiness level, exercise level, etc., may be monitored and/or used to improve employee productivity (e.g., by encouraging employees to rest, take a nap, relax, exercise more during a work day by taking the stairs, etc. if the received HRs indicate a need for the same).

Figure 4:
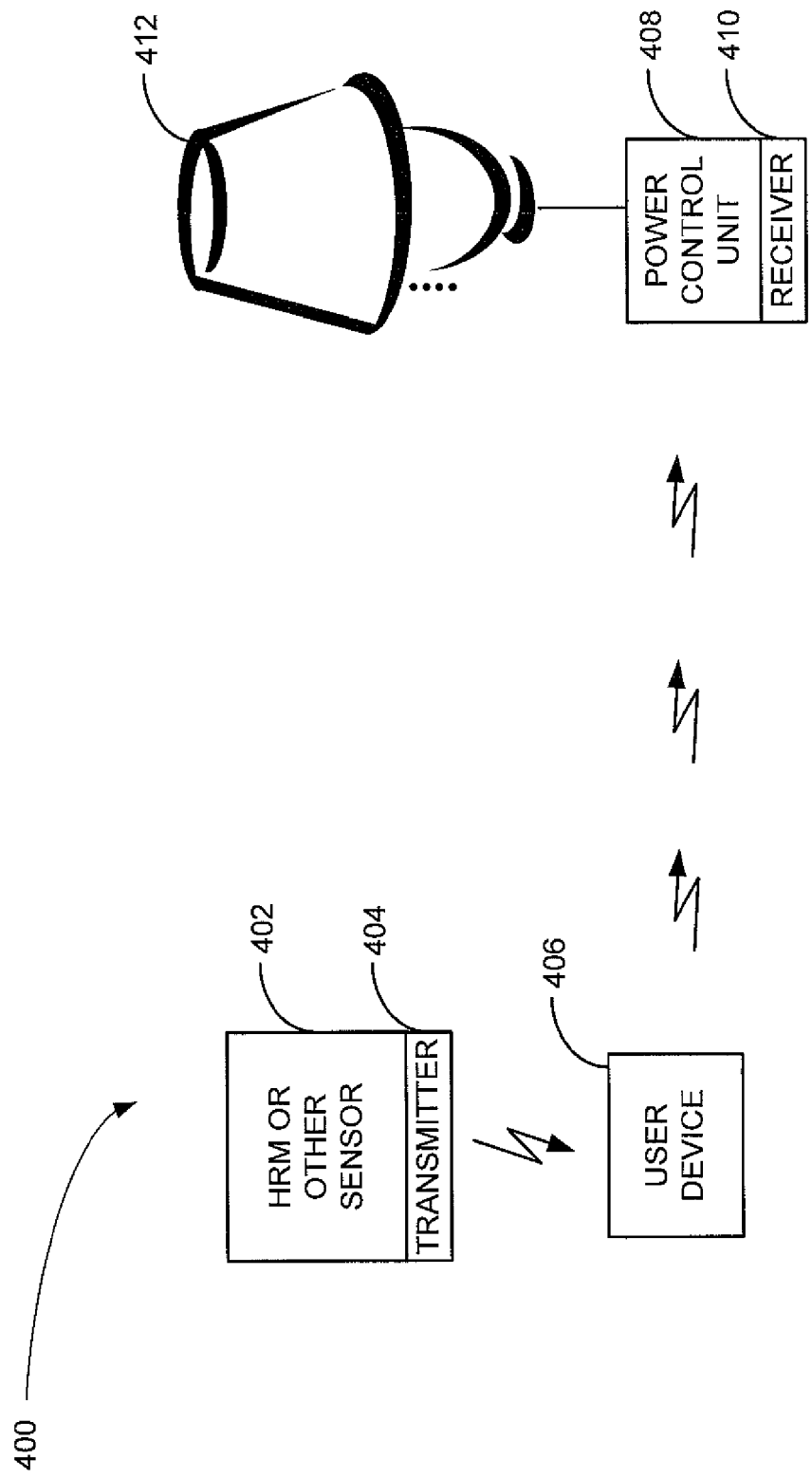
FIG. 4 is a schematic diagram of an alternative exemplary embodiment of the invention showing a system for controlling power delivery to an appliance using heart rate.

FIG. 4 is a schematic diagram of an alternative exemplary embodiment of the invention showing a system 400 for controlling power delivery to an appliance using heart rate. With reference to FIG. 4, the system 400 includes a HRM 402 or other sensor such as a heat flux sensor, a galvanic response sensor, etc., having a transmitter 404 adapted to transmit heart rate or other information to a user device 406 (e.g., a cellular telephone, PDA, laptop or desktop computer, etc.). The user device 406 is adapted to receive the information transmitted from the HRM or other sensor 402, process the information and use the information to control power delivery to an appliance. For example, as shown in FIG. 4, the user device 406 is adapted to communicate with a power delivery unit 408 (via a receiver 410), which controls power delivery to a lamp 412. The power delivery unit 408 may be capable of turning the lamp 412 on or off, and/or dimming the lamp 412 based on commands sent by the power deliver unit 408. Additional or other appliances may be similarly controlled such as televisions, radios, or the like. In some embodiments, the HRM or other sensor 402, user device 406 and power control unit 408 may communicate using Bluetooth™ or another wireless protocol. For instance, the transmitter 404 may be a Bluetooth™ transmitter, the user device 406 may be a Bluetooth™ capable cellular phone, PDA or computer, and/or the receiver 410 may be a Bluetooth™ receiver.

In one or more exemplary embodiments, the HRM 402 may monitor the heart rate of a user (e.g., via a wrist or chest strap), and transmit HR information to the user device 406. The user device 406 may examine the HR information and determine whether the user's HR is above a first predetermined value, and if so, allow the power control unit 408 to deliver electrical power to the lamp 412 (e.g., by sending the appropriate command, or sending no command). As the user relaxes, or meditates, the user's HR will slow down. After the user's HR drops below the first predetermined value, the user device 406 may transmit a command to the power control unit 408 instructing the power control unit 408 to either reduce the amount of power to the lamp 412, thus dimming the lamp 412, or stop delivering power to the lamp 412 (turning the lamp 412 off). Assuming the user device 406 only instructs the power control unit 408 to dim the lamp 412 as the user's HR drops below the first predetermined value, the user device 406 may instruct the power control unit 408 to further decrease power delivery to the lamp 412 as the user's HR decreases below additional lower threshold or HR values. In this manner, the user may control the amount of light delivered from the lamp 412 by controlling his/her heart rate (or another similar body function). The volume, channel and/or on/off state of a radio, TV, MP3 player, stereo or the like may be similarly controlled. As a further example, HR may be used to arm or disarm a house alarm.

In some embodiments, the HR or other sensor 402 may communicate directly with and/or control the power control unit 408. The user device 406 may be programmable, allowing a user to set HR thresholds, identify and/or select which appliances to control, etc. A user may set goals for HR to be reduced (e.g., turn off appliance, enable video game, enable purchased, etc.).

In some embodiments the present invention includes an HRM 104 adapted to monitor intentional changes in a user's HR and to allow the user 102 to use the intentional HR changes to wirelessly control user devices 106 without making any apparent or even perceptible motions or sounds. For example, a user 102 may concentrate on relaxing his body to intentionally slow his HR or the user 102 may concentrate on tensing his body to intentionally raise his HR. The user device 106 may be adapted to be controlled by the changes in the user's HR. For example, a user device 106 that includes a remote control for a television may be adapted to transmit a "channel up" signal, e.g., to a television when the HRM 104 signals that the user 102 has raised his HR by a predetermined incremental amount, e.g., 5 beats per minute, or over a specific threshold, e.g., >85 beats per minute. Likewise, the user device 106 that includes a remote control for a television may be adapted to transmit a "channel down" signal to a television when the HRM 104 signals that the user 102 has lowered his HR by a predetermined incremental amount, e.g., 5 beats per minute, or under a specific level, e.g., <80 beats per minute. In some embodiments, the user device 106 may include a user interface adapted to display HR information and provide the user feedback to make it easier for the user to control the user's HR. Further, the user interface may include an array of control options from which the user 102 may select a desired control function. The control options may be arranged so that the user 102 may move a selection indicator sequentially among the array of control options by increasing his HR and then he may select an option by decreasing his HR while the desired control option is selected. It may be difficult for a user 102 to precisely control his HR to an absolute level. However, the present invention facilitates an accurate degree of control by allowing the user to control devices based on relatively small incremental changes and/or based on HR directional change patterns, e.g., up 3 BPM, down 5 BPM, up 3 BPM.

While the present invention has been described primarily with reference to HR and HRMS, it will be understood that other body parameters may be measured and similarly used such as heat flow, galvanic skin response, etc. In at least one embodiment, a SenseWear® armband or Bodybugg™, available from BodyMedia, Inc. of Pittsburgh, Pa., may be modified and employed to deliver information to a user device in accordance with the present invention.

In some embodiments, the user device (e.g., such as a cellular telephone) may determine a sleep/awake state of a user based on signals from a heart rate monitor. The user device then may determine whether to direct an incoming call to voice mail based on the sleep/awake state of a user.

Accordingly, while the present invention has been disclosed in connection with the preferred embodiments thereof, it should be understood that other embodiments may fall within the spirit and scope of the invention, as defined by the following claims.

The invention claimed is:

1. A method of maintaining wakefulness of a driver of a vehicle using a cellular telephone and a wrist-worn heart rate monitor, comprising:
   providing a wrist-worn heart rate monitor having a wrist strap and a heart rate monitor including a sensor adapted to sense a heart rate of a user, and further including a transmitter adapted to wirelessly transmit a signal indicative of heart rate of the user;
   employing the wrist-worn heart rate monitor to measure a heart rate of a user while the user is driving a vehicle;
   communicating heart rate information from the wrist-worn heart rate monitor to the cellular telephone of the user while the user is driving the vehicle, the wrist-worn heart rate monitor and the cellular telephone paired to communicate and form a portable communicatively-coupled system that is at least configured to operate physically and electrically separate from the vehicle, and configured to monitor the wakefulness of the user while the user is driving the vehicle;
   employing the cellular telephone to determine when the user's heart rate is within an acceptable range for the user while the user is driving the vehicle, the acceptable range being based on being above a level that would indicate the user is about to fall asleep;
   in response to the user's heart rate being outside the acceptable range, employing the cellular telephone to attempt to alter the user's heart rate while the user is driving by prompting the user to respond in a manner that indicates an alertness level of the user; and
   increasing a frequency of determining whether the user's heart rate is within the acceptable range when the user's heart rate is close to an end of the acceptable range.

2. The method of claim 1 wherein the user's heart rate is raised by the cellular telephone using sound in response to the user's heart rate being below the acceptable range.

3. The method of claim 1 wherein the acceptable range depends on time of day.

4. The method of claim 1 wherein the acceptable range depends on traffic conditions.

5. The method of claim 1 wherein the acceptable range depends on weather conditions.

6. The method of claim 1 wherein the acceptable range depends on current vehicle speed.

7. The method of claim 1 wherein the acceptable range depends on health of the user.

8. The method of claim 1 wherein the acceptable range depends on age of the user.

9. The method of claim 1 wherein the acceptable range depends on medical history of the user.

10. The method of claim 1 wherein the acceptable range is based on being above a level that indicates the user is about to fall asleep and below a level that indicates the user is experiencing stress, and further comprising increasing a frequency of determining whether the user's heart rate is within the acceptable range in response to the user's heart rate being close to either end of the acceptable range.

11. The method of claim 1 wherein employing the cellular telephone to attempt to alter the user's heart rate while the user is driving includes directing the user to perform a task.

12. The method of claim 11 wherein the task includes at least one of adjusting radio volume, activating a turn signal and depressing a button.

13. The method of claim 11 wherein the task includes at least one of replying and pushing a button.

14. The method of claim 11 further comprising determining an alertness level of the user based on a time taken by the user to perform the task.

15. The method of claim 11 further comprising:
  employing the cellular telephone to determine if the user performed the task; and
  if the user failed to perform the task, employing the cellular telephone to perform an emergency procedure.

16. The method of claim 15 wherein the emergency procedure includes notifying a third party.

17. The method of claim 15 wherein the emergency procedure includes adjusting operation of the vehicle.

18. A system, comprising:
  a wrist-worn heart rate monitor including a sensor configured to sense a heart rate of a user, and further including and a transmitter configured to wirelessly transmit a signal indicative of heart rate of the user, wherein the wrist-worn heart rate monitor is configured to measure the heart rate of the user while the user is driving a vehicle and further configured to communicate heart rate information; and
  a cellular telephone configured to receive the heart rate information from the wrist-worn heart rate monitor while the user is driving the vehicle, the wrist-worn heart rate monitor and the cellular telephone paired to communicate and form a communicatively-coupled portable system that is at least configured to operate physically and electrically separate from the vehicle, and configured to monitor wakefulness of the user while the user is driving the vehicle, the cellular telephone including computer program code stored therein that, when executed by the cellular telephone, causes the cellular telephone to:
    determine when the user's heart rate is within an acceptable range for the user while the user is driving the vehicle, the acceptable range being based on being above a level that indicates the user is about to fall asleep;
    in response to a determination that the user's heart rate is outside the acceptable range, attempt to alter the user's heart rate while the user is driving by prompting the user to respond in a manner that indicates an alertness level of the user; and
    increase a frequency of determining when the user's heart rate is within the acceptable range when the user's heart rate is close to an end of the acceptable range.

19. The system of claim 18, wherein the computer program code stored in the cellular telephone, when executed by the cellular telephone, further causes the cellular telephone to attempt to alter the user's heart rate while the user is driving by directing the user to perform a task.

20. The system of claim 19, wherein the computer program code stored in the cellular telephone, when executed by the cellular telephone, further causes the cellular telephone to:
  determine whether the user performed the task; and
  if the user failed to perform the task, perform an emergency procedure.

21. The system of claim 18, wherein the acceptable range is based on being above a level that indicates the user is about to fall asleep, and below a level that indicates the user is experiencing stress.

* * * * *